United States Patent [19]

Mohrs et al.

[11] Patent Number: 5,262,566
[45] Date of Patent: Nov. 16, 1993

[54] PROCESS FOR THE PREPARATION OF OPTICALLY ACTIVE A-HYDROXYCARBOXYLIC ACIDS

[75] Inventors: Klaus-Helmut Mohrs, Wuppertal; Axel Carstens; Dieter Hoppe, both of Kiel, all of Fed. Rep. of Germany

[73] Assignee: Bayer Aktiengesellschaft, Leverkusen, Fed. Rep. of Germany

[21] Appl. No.: 988,569

[22] Filed: Dec. 10, 1992

[30] Foreign Application Priority Data

Dec. 20, 1991 [DE] Fed. Rep. of Germany ....... 4142190

[51] Int. Cl.$^5$ .................... C07C 59/40; C07D 263/52
[52] U.S. Cl. ................................... 562/468; 548/216; 548/239
[58] Field of Search ................ 562/468; 548/216, 239

[56] References Cited

U.S. PATENT DOCUMENTS

| | | | |
|---|---|---|---|
| 4,467,095 | 8/1984 | Treves | 546/342 |
| 4,703,052 | 10/1987 | Eggler et al. | 514/337 |
| 4,738,972 | 4/1988 | Eggler et al. | 514/314 |
| 4,970,215 | 11/1990 | Mohrs et al. | 514/311 |

FOREIGN PATENT DOCUMENTS

| | | |
|---|---|---|
| 309425 | 3/1989 | European Pat. Off. |
| 2046659 | 3/1972 | Fed. Rep. of Germany |
| 549796 | 3/1986 | Spain |
| 1015024 | 12/1965 | United Kingdom |

OTHER PUBLICATIONS

J. Org. Chem. 24 (1959), 1301, 1308.
J. Med. Chem. 31 (1), 37-54 1988.
J. Med. Chem. 34 (10), 2962-2983 1991.
Verweij A. J. Chromatogr. 69 (2) 407-10 1972.
Armstrong, D. et al Science 232 (4754, Pt. 1) 1132-5 1986.
Schjelderup, L et al Acta Chem. Scand. Ser B B40 (7) 601-3 1986.
Barlow, R. B et al J. Med. Chem 16 (5) 439-46 1973.
Rakin, D et al, Noucno-Teh. Pregl. 29(1) 3-10 1979.
Young, J. M., J. Pharm. Pharmacol. 24(12) 950-4 1972.
Inch, T. D., J. Pharm. Pharmacol. 23(10) 813-15 1971.

*Primary Examiner*—Paul J. Killos
*Attorney, Agent, or Firm*—Sprung Horn Kramer & Woods

[57] ABSTRACT

The invention relates to a process for the preparation of optically active α-hydroxycarboxylic acids characterised in that carbamates are first reacted in the presence of a selective base and of a chelate-forming diamine to give a carbanion complex compound, this is then dia- or enantioselectively deprotonated, then substituted with $CO_2$ and, as a final step, the heterocyclic protective group is eliminated.

10 Claims, No Drawings

PROCESS FOR THE PREPARATION OF OPTICALLY ACTIVE A-HYDROXYCARBOXYLIC ACIDS

The invention relates to a new process for the preparation of optically active α-hydroxycarboxylic acids, some of which are known, which are important intermediates for the synthesis of pharmaceutical active compounds, in particular for the synthesis of lipoxygenase inhibitors.

α-Hydroxycarboxylic acids are known from a large number of publications [cf., for example, J. Org. Chem. 24 (1957), 1301, 1308; U.S. Pat. No. 1,352,332 (1964)].

Moreover, it is known that the processes for their preparation have great disadvantages because large amounts of bases are employed and the elimination of protective groups is difficult, which results in a low yield.

The present invention now relates to a process for the preparation of optically active α-hydroxycarboxylic acids of the general formula (I)

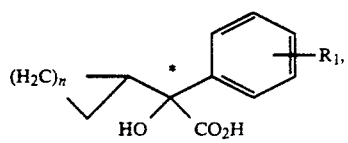

in which
n represents a number 1, 2, 3, 4, 5 or 6 and
$R^1$ represents hydrogen, halogen or straight-chain or branched alkyl having up to 6 carbon atoms, or a radical of the formula —O—T,
in which
T is straight-chain or branched alkyl having up to 6 carbon atoms or a typical hydroxyl protective group,
characterised in that carbamates of the general formula (II)

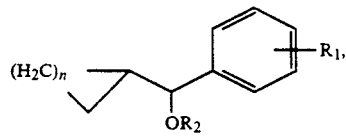

in which
n and $R^1$ have the abovementioned meaning, and
$R^2$ represents a radical of the formula

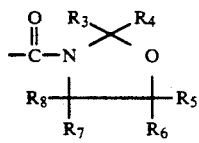

in which
$R^3$, $R^4$, $R^5$, $R^6$, $R^7$ and $R^8$ are identical or different and represent hydrogen, straight-chain or branched alkyl having up to 8 carbon atoms, phenyl or cycloalkyl having 3 to 6 carbon atoms, or in each case $R^3$ and $R^4$, $R^5$ and $R^6$ and/or $R^7$ and $R^8$ together form a 3- to 6-membered saturated carbocycle, are deprotonated dia- or enantioselectively, first in inert solvents, in the presence of a selective base, preferably sec.-butyllithium, and of a chelate-forming diamine (termed D hereinafter) to give the carbanion complex compounds of the general formula (III)

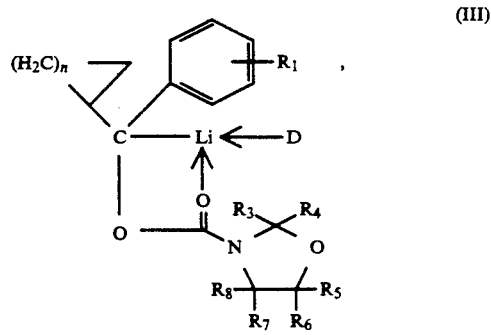

in which
n, $R^1$, $R^3$, $R^4$, $R^5$, $R^6$, $R^7$ and $R^8$ have the abovementioned meaning,
and
D represents chelate-forming diamines such as, for example, (−)-spartein or TMEDA,
and the products are subsequently converted directly by electrophilic substitution with $CO_2$ in inert solvents into the compounds of the general formula (IV)

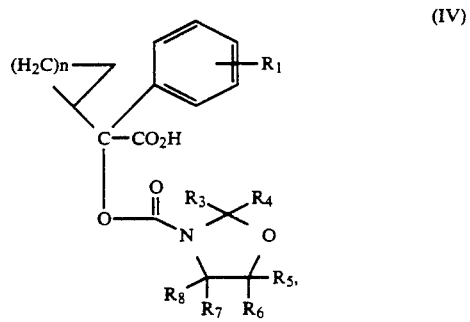

in which
n, $R^1$, $R^3$, $R^4$, $R^5$, $R^6$, $R^7$ and $R^8$ have the abovementioned meaning,
or these are first converted with diazomethane in ether into the compounds of the general formula (V)

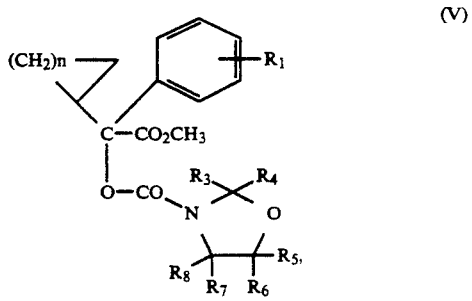

in which
n, $R^1$, $R^3$, $R^4$, $R^5$, $R^6$, $R^7$ and $R^8$ have the abovementioned meaning, and, in a last step, the heterocyclic protective group is eliminated by customary methods and the methyl radicals are hydrolysed by the customary method.

The process according to the invention can be illustrated by way of example by the following equation:

n represents a number 1, 2, 3, 4, 5 or 6, and
R¹ represents hydrogen, fluorine, chlorine or straight-chain or branched alkyl having up to 4 carbon atoms or a radical of the formula—O—T,
in which

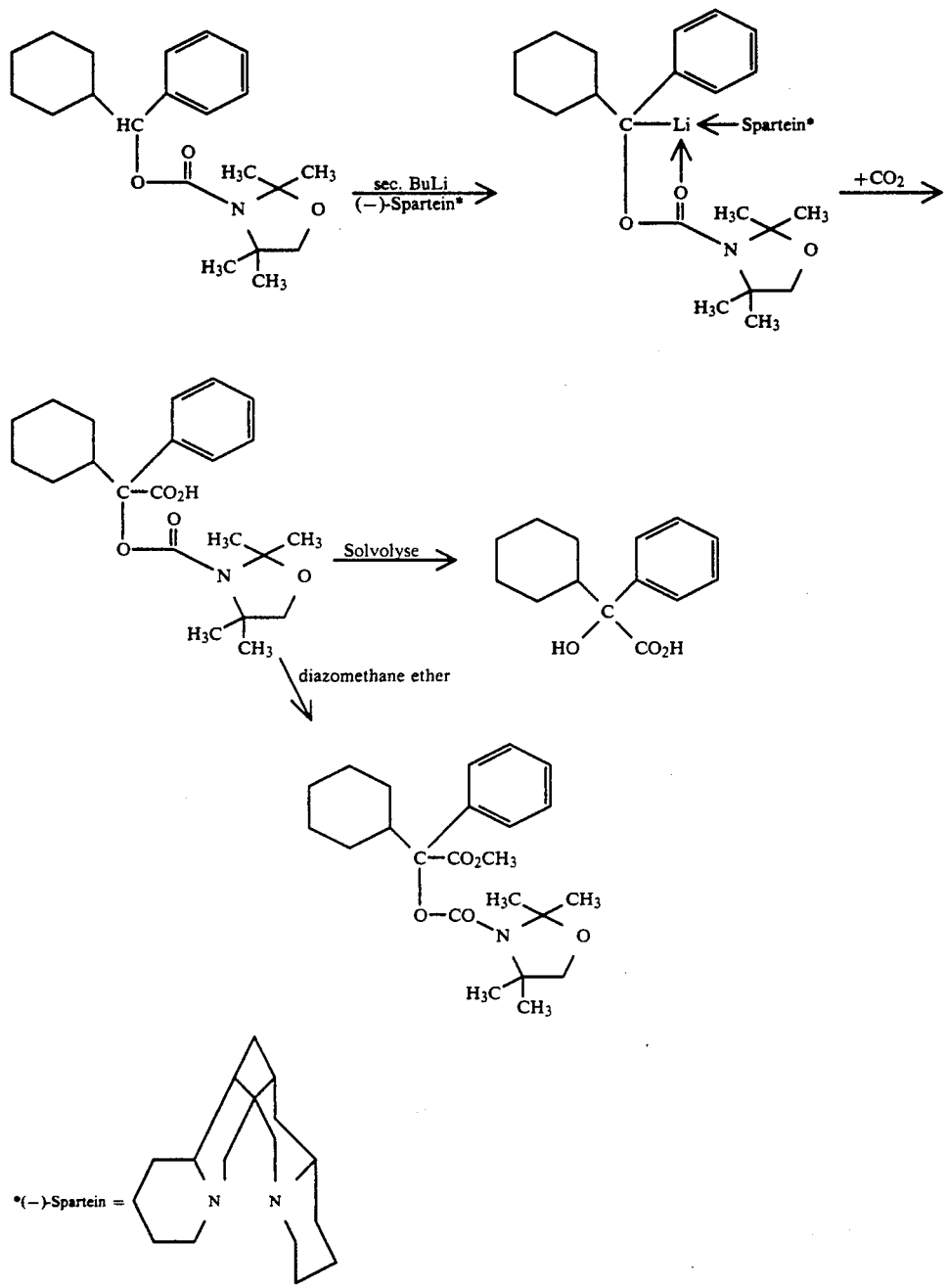

Hydroxyl protective group within the scope of the abovementioned definition generally represents a protective group from the series comprising: trimethylsilyl, triethylsilyl, triisopropylsilyl, tert.butyl-dimethylsilyl, tert.-butyldiphenylsilyl, triphenylsilyl, trimethylsilylethoxycarbonyl, methoxymethyl or benzoyl. Benzoyl, trimethylsilyl or tert.butyl-dimethylsilyl are preferred.

Compounds which are preferably prepared by the process according to the invention are those of the general formula (I) in which T represents straight-chain or branched alkyl having up to 4 carbon atoms, benzoyl, trimethylsilyl or tert.butyldimethylsilyl.

Compounds which are particularly preferably prepared by the process according to the invention are those of the general formula (I) in which
n represents a number 1, 2, 3, 4, 5 or 6, and
R¹ represents hydrogen, methyl, chlorine or a radical of the formula —O—T,
in which T represents methyl, ethyl, benzoyl, trimethylsilyl or tert.butyldimethylsilyl.

Solvents which are preferably suitable for the deprotonating step are inert organic solvents such as hydrocarbons such as hexane, pentane, ligroin or toluene, and ethers, for example tetrahydrofuran, diethyl ether, dioxane, dimethoxyethane, diglyme, triglyme or tert.-butyl methyl ether. Tetrahydrofuran and diethyl ether are particularly preferred.

The deprotonating step is carried out in a temperature range of from $-100°$ C. up to room temperature, preferably at approx. $-78°$ C. to $0°$ C.

The deprotonating step can be carried out at atmospheric pressure as well as under increased or reduced pressure (for example 0.5 to 2 bar), preferably under atmospheric pressure.

Suitable selective bases are alkyllithium compounds having up to 6 C atoms in the alkyl group, preferably n-butyllithium or sec.-butyllithium.

The base is employed in an amount of from 0.5 to 5 moles, preferably in stoichiometric amounts, per mole of the compounds of the general formula (II).

The electrophilic substitution with $CO_2$ is equally carried out in the abovementioned solvents, preferably in tetrahydrofuran, under atmospheric pressure.

The esterification with diazomethane is carried out in ether at room temperature.

The elimination is carried out by the customary method by sequential treatment with acids and bases in one of the abovementioned solvents, preferably in methanol.

Suitable acids are strong inorganic acids and organic sulphonic or carboxylic acids such as, for example, methanesulphonic acid, ethanesulphonic acid, benzenesulphonic acid, toluenesulphonic acid, acetic acid or propionic acid.

Suitable bases are alkali metal hydroxides and alkaline earth metal hydroxides such as, for example, sodium hydroxide, potassium hydroxide or barium hydroxide. Barium hydroxide is preferred.

The acids and bases are employed in an amount of from 0.01 to 10 moles, preferably 1 mole, per mole of the compounds of the general formula (IV).

The elimination is effected under atmospheric pressure in a temperature range of from $0°$ C. to $+130°$ C., preferably from $+20°$ C. to $+100°$ C.

The elimination can also be effected using lithium-aluminium hydride in one of the abovementioned solvents, preferably tetrahydrofuran.

The carboxylates are hydrolysed by customary methods, by treating the esters with customary bases in inert solvents.

Bases which are suitable for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate, or sodium hydrogen carbonate. Sodium hydroxide or potassium hydroxide are particularly preferably employed.

Suitable solvents for the hydrolysis are water or the organic solvents which are customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to use mixtures of the abovementioned solvents.

The esterification is generally carried out in a temperature range of from $0°$ C. to $+100°$ C., preferably from $+20°$ C. to $+80°$ C.

In general, the esterification is carried out under atmospheric pressure. However, it is also possible to carry out the process under subatmospheric or superatmospheric pressure (for example from 0.5 to 5 bar).

When carrying out the hydrolysis, the base is generally employed in an amount of from 1 to 3 moles, preferably from 1 to 1.5 moles, per mole of the ester. Molar amounts of the reactants are particularly preferably used.

The compounds of the general formula (II) are new and can be prepared by reacting compounds of the general formula (VI)

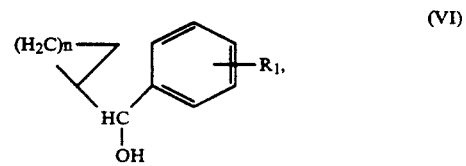

in which n and $R^1$ have the abovementioned meaning with compounds of the general formula (VII)

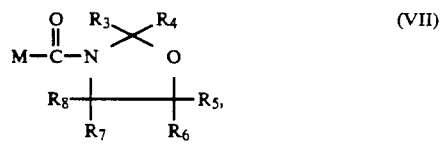

in which $R^3$, $R^4$, $R^5$, $R^6$, $R^7$ and $R^8$ have the abovementioned meaning and M represents halogen, preferably chlorine, in one of the abovementioned organic solvents, preferably diethyl ether, in the presence of a base, preferably sodium hydride, or benzyl chloroformate derivatives of the general formula (VIII)

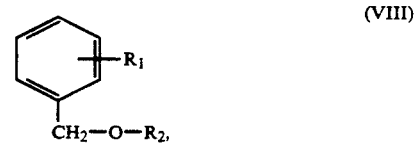

in which $R^1$ and $R^2$ have the abovementioned meaning, are first treated with TMEDA in one of the abovementioned solvents, preferably in tetrahydrofuran, subsequently deprotonated in hexane using butyllithium, and, in a final step, alkylated using compounds of the general formula (IX)

in which

X represents halogen, preferably iodine.

The deprotonation is carried out at −78° C. and atmospheric pressure.

The alkylation is carried out in the temperature range from −78° C. to +40° C.

Some of the compounds of the general formula (VIII) are new and can be prepared by reacting the corresponding benzyl chloroformate derivatives with the oxazoline derivatives in ethers in a temperature range of from −20° C. to +10° C., preferably at 0° C. and atmospheric pressure.

The cycloalkyl halides of the general formula (IX) are known.

Some of the compounds of the general formulae (VI) and (VII) are known or can be prepared by customary methods [cf. J. Med. Chem. 31 (1), 37–54; 34 (10), 2962–83; PCT WO 86/07056].

Surprisingly, the enantioselective process according to the invention yields the desired compounds of the general formula (I) in good yields.

The process is distinguished by a series of advantages: as opposed to the prior art, stoichiometric amounts of bases, preferably sec.-butyllithium, suffice for the deprotonation. Moreover, the process according to the invention allows the diastereoselectivity to be controlled when optically active alcohols are used.

The use of chiral (−)-spartein causes the enantioselective deprotonation of the compounds of the formula (II) in very good yields to give the corresponding chiral compounds, preferably the (S)-lithium compounds of the formula (III), which can be converted by further reaction with $CO_2$, preferably in the R configuration.

The compounds according to the invention are also characterised in that the protective group $R^2$ can be eliminated very easily after the enantioselective introduction of the electrophile ($CO_2$), forming the free hydroxyl group. The compounds of the general formulae (III), (IV) and (V) are new and can be prepared by the process described above.

Thus, the process according to the invention allows optically active α-hydroxycarboxylic acids, which are valuable intermediates for the synthesis of lipoxygenase-inhibiting active compounds [cf. EP 344,519], to be obtained in an elegant manner and in good yields.

EXAMPLE 1

Benzyl 2,2,4,4-tetramethyl-oxazolidine-3-carboxylate

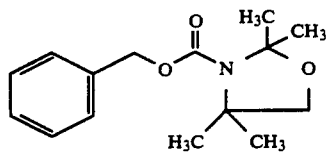

8,500 g (50.00 mmol) of benzyl chloroformate were dissolved in 100 ml of dry ether, and the solution was added slowly with ice-cooling to a solution of 12,800 g (100.00 mmol) of the oxazolidine in 100 ml of dry ether. The ice-cooling was removed, and refluxing was continued for a further hour. Aqueous work-up and purification on silica gel (ether/petroleum ether 1:10) gave 11,967 g (45.50 mmol) of the title compound, which was 91%. $R_f$ 0.51 (ether/petroleum ether 1:5).

EXAMPLE 2

Cyclohexyl-phenyl-methyl 2,2,4,4-tetramethyl-1,3-oxazolidine-3-carboxylate

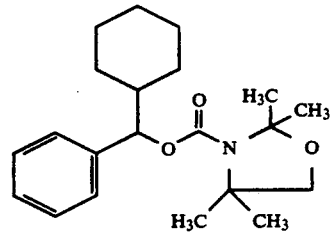

2,630 g (10.00 mmol) of the compound of Example 1 were dissolved in 10 ml of dry THF and the mixture was treated with 1,160 g (10.00 mmol) of TMEDA. After the mixture had been cooled to −78° C., it was deprotonated using 6.3 ml (100.00 mmol) of an approx. 1.6M n-butyllithium solution in hexane. After approx. 30 minutes, 4,200 g (20 mmol) of cyclohexyl iodide were added. After 4 hours, the mixture was brought to room temperature and subjected to aqueous work-up. Purification on silica gel (ether/ petroleum ether 1:9) gave 2,736 g (7.90 mmol) of the title compound, which was 79%.

$R_f$ 0.56 (ether/petroleum ether 1:3).

EXAMPLE 3

Cyclooctyl-phenyl-methyl 2,2,4,4-tetramethyl-1,3-oxazolidine-3-carboxylate

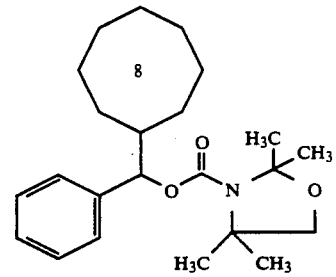

2,630 g (10.00 mmol) of the compound of Example 1 were dissolved using 1,160 g (10.00 mmol) of TMEDA in 10 ml of dry THF, and the solution was cooled to −78° C. 6.3 ml (100 mmol) of an approx. 1.6M n-butyllithium solution in hexane were added, and stirring of the mixture was then continued for 30 minutes before 4,760 g (20.00 mmol) of cyclooctyl iodide were added. After 5 hours, the mixture was allowed to come to room temperature and worked up in an aqueous medium. Purification on silica gel (ether/petroleum ether 1:9) gave 2,540 g (6.80 mmol) of the title compound, which was 68%. $R_f$ 0.52 (ether/petroleum ether 1:3).

EXAMPLE 4

Methyl (2-cyclohexyl-2-phenyl)-(2,2,4,4-tetramethyl-1,5-oxazolidine-2-carbonyloxy)-acetate

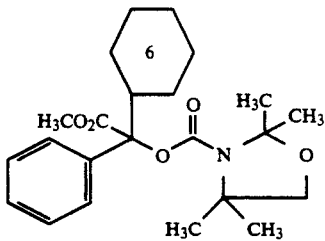

690 mg (2.00 mmol) of the compound of Example 2 and 235 mg (1.00 mmol) of (−)-spartein were dissolved in 2 ml of dry ether, and the solution was cooled to −78° C. 0.73 ml (1.00 mmol) of a sec.-butyllithium solution in cyclohexane/hexane was added, and the mixture was stirred for 24 hours. A stream of dry $CO_2$ was then passed into the solution for 10 minutes. After 1 hour, the mixture was allowed to come to room temperature and subjected to acidic work-up, and the organic phase was dried over magnesium sulphate. The solution was filtered and then concentrated in vacuo, and a solution of diazomethane ether was added until the solution remained a yellow colour. After 2 hours, excess diazomethane was destroyed using silica gel, and the residue, which was obtained after concentration in vacuo, was chromatographed on silica gel (ether/petroleum ether 1:6). Besides 369 g (1.07 mmol) of . . ., which was 53%, 200 mg (0.50 mmol) of the title compound, which was 25%, were also obtained.

$R_f$ 0.36 (ether/petroleum ether 1:3).

EXAMPLE 5

Methyl 2-cyclooctyl-2-phenyl-(2,2,4,4-tetramethyl-1,3-oxazolidine-3-carbonyloxy)-acetate

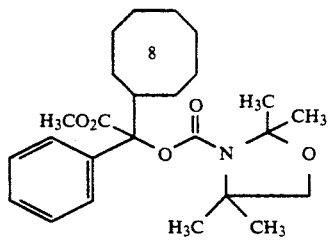

The preparation was analogous to the procedure of Example 4. 220 mg (0.51 mmol) of the title compound, which was 25%, were obtained.

$R_f$ 0.34 (ether/petroleum ether 1:3).

EXAMPLE 6

Cyclohexyl-(4-methoxy-phenyl)-methyl 2,2,4,4-tetramethyl-1,3-oxazolidine-3-carboxylate

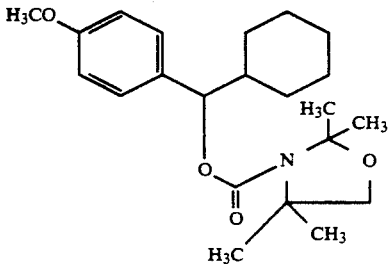

660 mg (3.00 mmol) of the alcohol were added at room temperature to a suspension of 90.0 mg (3.00 mmol) of sodium hydride (80% suspension in paraffin oil) in 20 ml of dry DnE. The mixture was stirred for 5 days at room temperature. 576 mg (3.00 mmol) of the carbamoyl chloride dissolved in DnE (10 ml) were then added to the mixture, and stirring was continued for 5 days. After aqueous work-up and purification on silica gel (ether/petroleum ether 1:3) 202 mg (0.54 mmol) of the title compound, which was 18%, were obtained.

$R_f$ 0.48 (ether/petroleum ether 1:5)

We claim:

1. Process for the preparation of optically active α-hydroxycarboxylic acids of the general formula

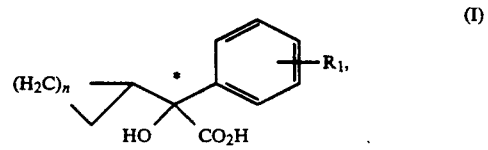

in which n represents a number 1, 2, 3, 4, 5 or 6 and $R^1$ represents hydrogen, halogen or straight-chain or branched alkyl having up to 6 carbon atoms, or a radical of the formula —O—T, in which T is straight-chain or branched alkyl having up to 6 carbon atoms or a typical hydroxyl protective group, characterised in that carbamates of the general formula (II)

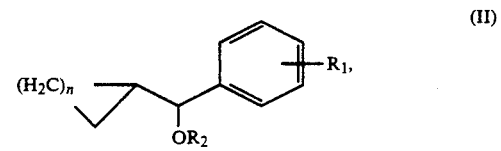

in which n and $R^1$ have the abovementioned meaning, and $R^2$ represents a radical of the formula

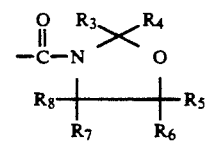

in which $R^3$, $R^4$, $R^5$, $R^6$, $R^7$ and $R^8$ are identical or different and represent hydrogen, straight-chain or branched alkyl having up to 8 carbon atoms, phenyl or cycloalkyl having 3 to 6 carbon atoms, or in each case $R^3$ and $R^4$, $R^5$ and $R^6$ and/or $R^7$ and $R^8$ together form a 3- to 6-membered saturated carbocycle, are deprotonated dia- or enantioselectively, first in inert solvents, in the presence of a selective base, preferably sec.-butyllithium, and of a chelate-forming diamine (termed D hereinafter) to give the carbanion complex compounds of the general formula (III)

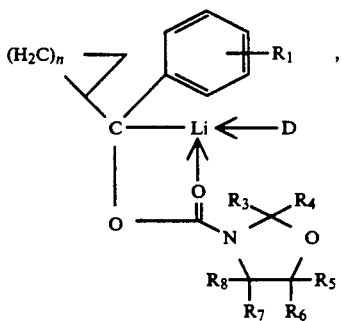

(III)

in which n, $R^1$, $R^3$, $R^4$, $R^5$, $R^6$, $R^7$ and $R^8$ have the abovementioned meaning, and D represents chelate-forming diamines such as, for example, (−)-spartein or TMEDA, and the products are subsequently converted directly by electrophilic substitution with $CO_2$ in inert solvents into the compounds of the general formula (IV)

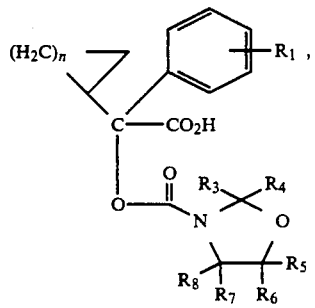

(IV)

in which n, $R^1$, $R^3$, $R^4$, $R^5$, $R^6$, $R^7$ and $R^8$ have the abovementioned meaning, or these are first converted with diazomethane in ether into the compounds of the general formula (V)

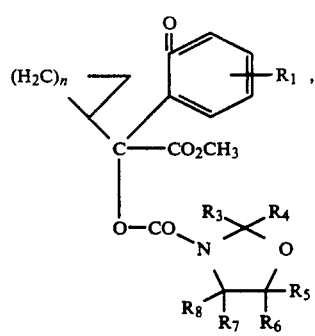

(V)

in which n, $R^1$, $R^3$, $R^4$, $R^5$, $R^6$, $R^7$ and $R^8$ and have the abovementioned meaning, and, in a last step, the heterocyclic protective group is eliminated by customary methods and the methyl radicals are hydrolysed by the customary method.

2. Process according to claim 1 for the preparation of compounds of the formula (I) in which n represents a number 1, 2, 3, 4, 5 or 6, and $R^1$ represents hydrogen, fluorine, chlorine or straight-chain or branched alkyl having up to 4 carbon atoms or a radical of the formula —O—T, in which T represents straight-chain or branched alkyl having up to 4 carbon atoms, benzoyl, trimethylsilyl or tert.butyldimethylsilyl.

3. Process according to claim 1 for the preparation of compounds of the formula (I) according to claim 1, in which n represents a number 1, 2, 3, 4, 5 or 6, and $R^1$ represents hydrogen, methyl, chlorine or a radical of the formula —O—T, in which T represents methyl, ethyl, benzoyl, trimethylsilyl or tert.butyldimethylsilyl.

4. Process according to claim 1, characterised in that the deprotonation is carried out in a temperature range of from −100° C. to room temperature.

5. Process according to claim 1, characterised in that alkyllithium compounds having up to 6 carbon atoms in the alkyl group are employed as selective base.

6. Process according to claim 1, characterised in that the elimination is carried out in a temperature range of from 0° C. to +130° C.

7. Process according to claim 1, characterised in that the elimination is carried out using lithium-aluminium hydride.

8. Carbamates of the general formula (II)

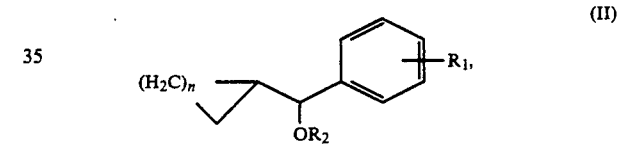

(II)

in which n represents a number 1, 2, 3, 4, 5 or 6, $R^1$ represents hydrogen, halogen or straight-chain or branched alkyl having up to 6 carbon atoms, or a radical of the formula —O—T, which T represents straight-chain or branched alkyl having up to 6 carbon atoms or a typical hydroxyl protective group, and $R^2$ represents a radical of the formula

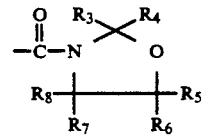

in which $R^3$, $R^4$, $R^5$, $R^6$, $R^7$ and $R^8$ are identical or different and represent hydrogen, straight-chain or branched alkyl having up to 8 carbon atoms, phenyl or cycloalkyl having 3 to 6 carbon atoms, or in each case $R^3$ and $R^4$, $R^5$ and $R^6$ and/or $R^7$ and $R^8$ together form a 3- to 6-membered saturated carbocycle.

9. Carbanion complex compounds of the general formula (III)

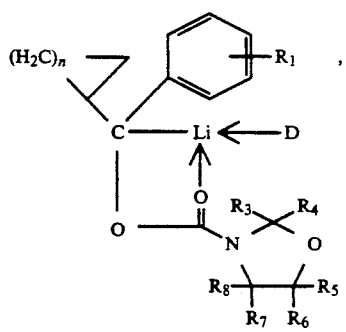

(III)

in which n represents a number 1, 2, 3, 4 or 5, $R^1$ represents hydrogen, halogen or straight-chain or branched alkyl having up to 6 carbon atoms, or represents a radical of the formula —O—T in which T represents straight-chain or branched alkyl having up to 6 carbon atoms or a typical hydroxyl protective group, D represents chelate-forming diamines such as, for example, (−)-spartein or TMEDA, and $R^3$, $R^4$, $R^5$, $R^6$, $R^7$ and $R^8$ are identical or different and represent hydrogen, straight-chain or branched alkyl having up to 8 carbon atoms, phenyl or cycloalkyl having 3 to 6 carbon atoms, or in each case $R^3$ and $R^4$, $R^5$ and $R^6$ and/or $R^7$ and $R^8$ together form a 3- to 6-membered saturated carbocycle.

10. Compounds of the general formula (IV)

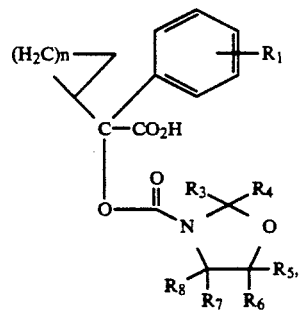

(IV)

in which n represents a number 1, 2, 3, 4, 5 or 6, $R^1$ represents hydrogen, halogen or straight-chain or branched alkyl having up to 6 carbon atoms, or represents a radical of the formula —O—T in which T represents straight-chain or branched alkyl having up to 6 carbon atoms or a typical hydroxyl protective group, and $R^3$, $R^4$, $R^5$, $R^6$, $R^7$ and $R^8$ are identical or different and represent hydrogen, straight-chain or branched alkyl having up to 8 carbon atoms, phenyl or cycloalkyl having 3 to 6 carbon atoms, or in each case $R^3$ and $R^4$, $R^5$ and/or $R^6$ $R^7$ and $R^8$ together form a three- to six-membered carbocycle.

* * * * *